(12) United States Patent
Johnston

(10) Patent No.: US 8,142,255 B2
(45) Date of Patent: *Mar. 27, 2012

(54) BRA PAD AND METHOD OF RELIEVING BREAST ENGORGEMENT

(76) Inventor: Sharon Johnston, Nine Mile Falls, WA (US)

( * ) Notice: Subject to any disclaimer, the term of this patent is extended or adjusted under 35 U.S.C. 154(b) by 223 days.

This patent is subject to a terminal disclaimer.

(21) Appl. No.: 12/476,493

(22) Filed: Jun. 2, 2009

(65) Prior Publication Data

US 2010/0069869 A1 Mar. 18, 2010

Related U.S. Application Data

(63) Continuation-in-part of application No. 12/233,235, filed on Sep. 18, 2008.

(51) Int. Cl.
*A41C 3/00* (2006.01)
(52) U.S. Cl. ............................................ 450/37; 450/54
(58) Field of Classification Search .............. 450/37–39, 450/54–58; 2/267, 268
See application file for complete search history.

(56) References Cited

U.S. PATENT DOCUMENTS

| | | | |
|---|---|---|---|
| 1,527,009 A | 2/1928 | Plate | |
| 2,125,620 A | 8/1938 | Schlumbohm | |
| 4,675,009 A | 6/1987 | Hymes et al. | |
| 5,018,521 A | 5/1991 | Campbell | |
| 5,326,305 A * | 7/1994 | Fochler | 450/57 |
| 5,839,942 A | 11/1998 | Miller | |
| 6,241,715 B1 * | 6/2001 | Houser et al. | 604/385.07 |
| 6,916,334 B2 * | 7/2005 | Noonan | 607/108 |
| 6,945,966 B2 * | 9/2005 | Mikami | 604/346 |
| 7,241,797 B2 * | 7/2007 | Horseman | 514/412 |
| 2003/0013145 A1 | 1/2003 | Titmas | |
| 2003/0220048 A1 | 11/2003 | Toro et al. | |
| 2006/0046616 A1 | 3/2006 | Alessi | |
| 2006/0052033 A1 | 3/2006 | Foley et al. | |
| 2007/0014881 A1 | 1/2007 | Harder-Tolar | |
| 2007/0015438 A1 | 1/2007 | Lange et al. | |
| 2007/0099542 A1 * | 5/2007 | Sakaguchi et al. | 450/37 |
| 2008/0140040 A1 * | 6/2008 | Kawakami et al. | 604/385.07 |
| 2008/0160115 A1 | 7/2008 | Shaked et al. | |

OTHER PUBLICATIONS

WO PCT/US2009/055609, Mar. 25, 2010, Sharon Johnston, Written Opinion.

* cited by examiner

*Primary Examiner* — Gloria Hale
(74) *Attorney, Agent, or Firm* — Wells St. John, P.S.

(57) ABSTRACT

A pad for relieving breast engorgement includes a material comprising absorbent fibers and an acidic agent. The pad is configured to insert within the cup of a bra. A bra pad has a layer of absorbent fiber material with a front surface and a back surface. A liquid barrier layer has a first side interfacing the back surface of the absorbent fiber material and an opposing second side. An acidic agent is disposed within the absorbent fiber material. A method of relieving breast engorgement includes providing an absorbent pad including absorbent fibers and an acidic agent shaped to insert within a cup of a bra and disposing the pad between the cup of the bra and an engorged breast to be relieved.

26 Claims, 5 Drawing Sheets

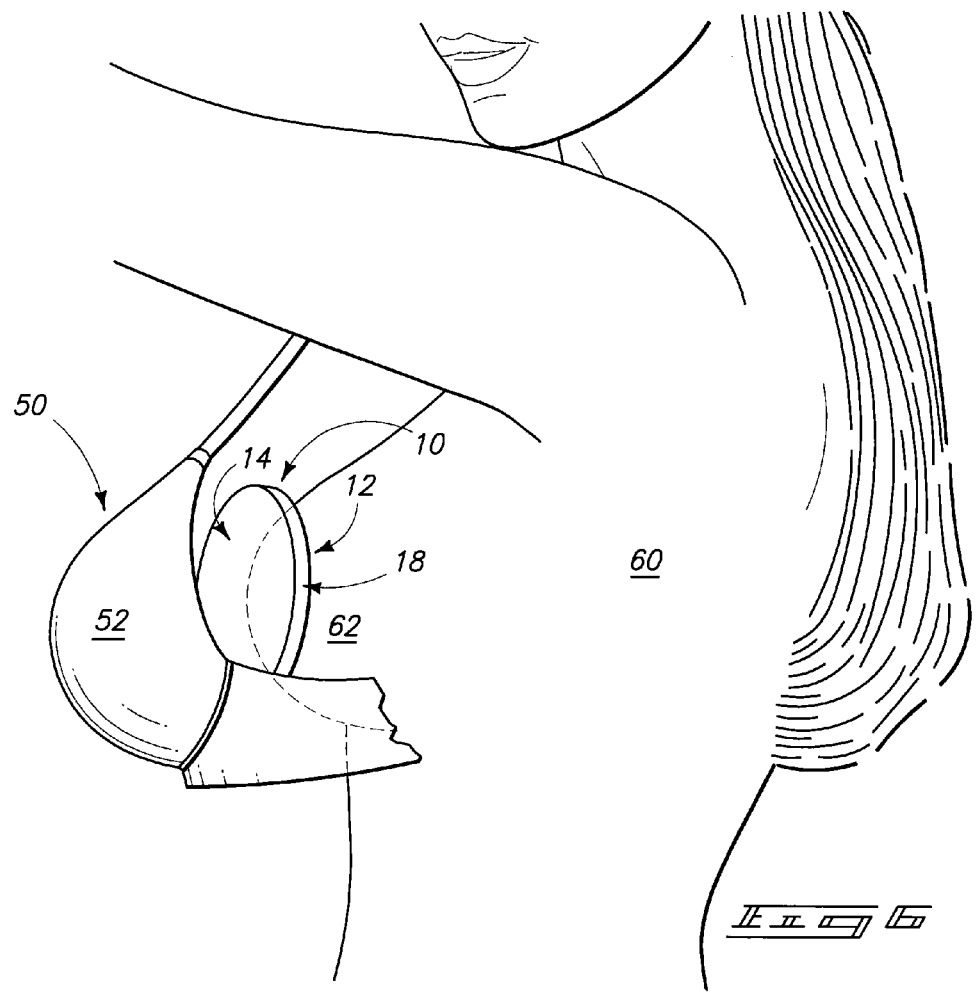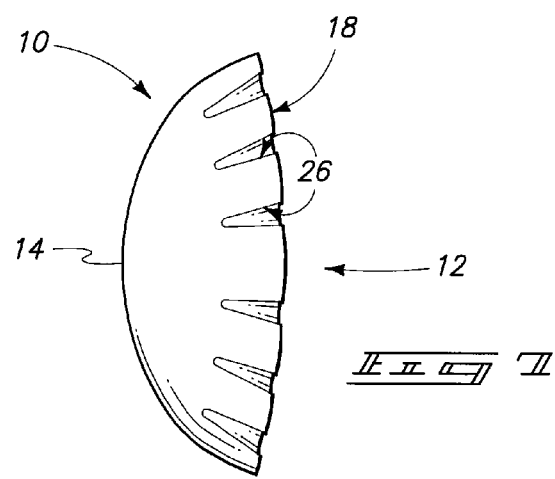

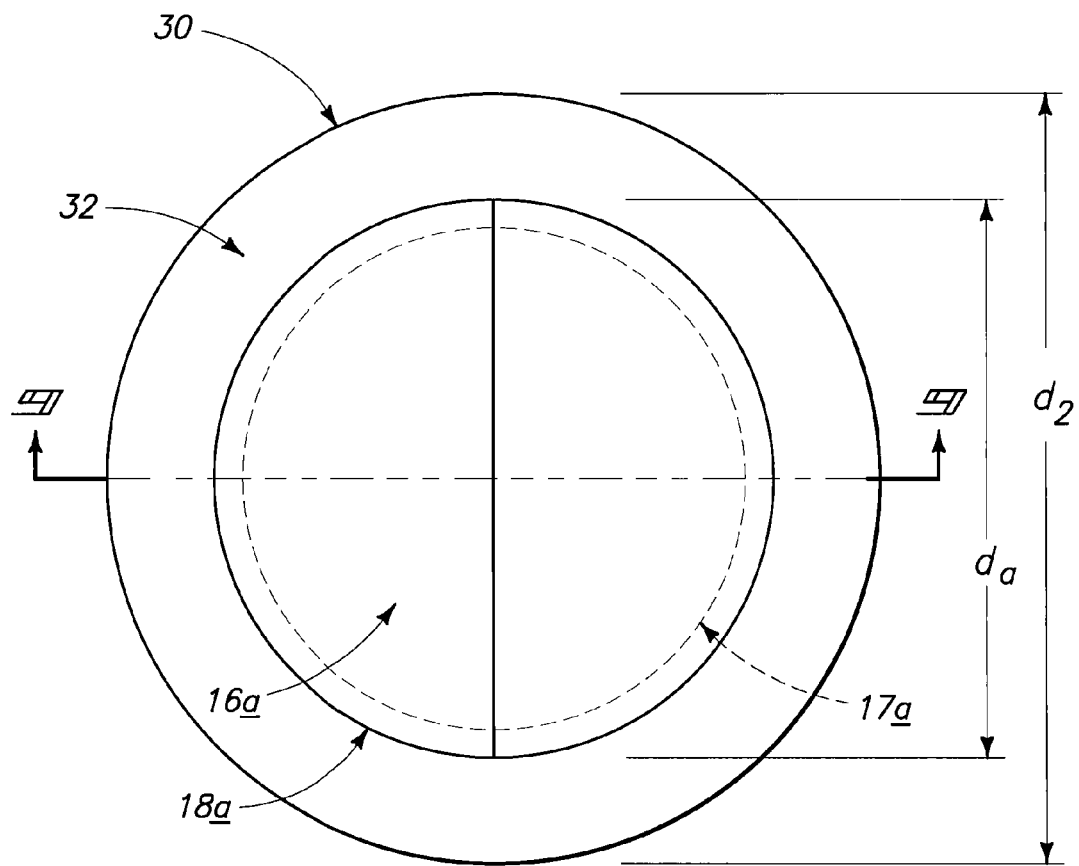
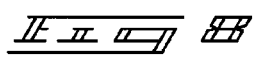
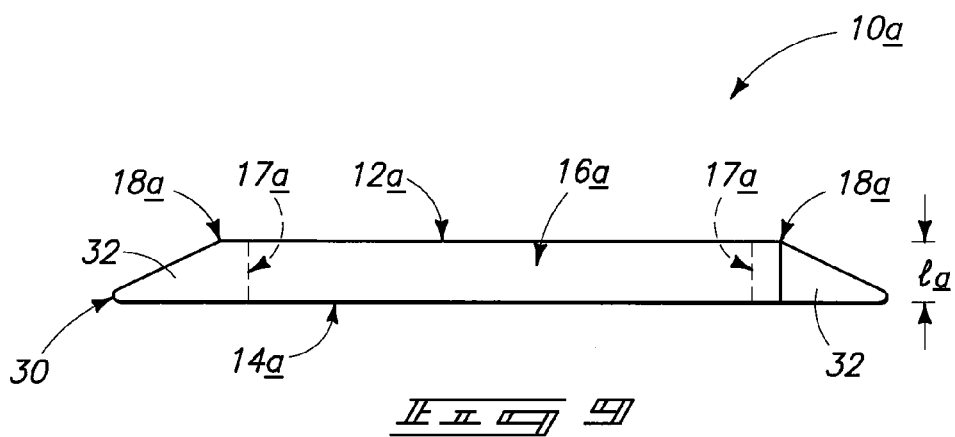

BRA PAD AND METHOD OF RELIEVING BREAST ENGORGEMENT

RELATED PATENT DATA

This patent resulted from a continuation-in-part of U.S. patent application Ser. No. 12/233,235 filed Sep. 18, 2008.

TECHNICAL FIELD

The invention pertains to a pad for relieving breast engorgement, a bra pad, and a method of relieving breast engorgement.

BACKGROUND OF THE INVENTION

Breast engorgement is an overfilling of the breast with milk. This condition may be accompanied by breast swelling, hardness, heat and/or throbbing, and may cause mild to severe pain. Engorgement can occur when an infant is not removing sufficient amounts of milk from the breast, such as shortly after birth, failure of the infant to latch on well, during infant illness, or during transition to solid foods during weaning. Engorgement can also occur when a mother chooses not to breast feed her newborn. Engorgement can occur in one or both breasts.

To date there have been very few treatments for breast engorgement. Treatments such as cold packs, baths, and massage have been recommended to treat symptoms of engorgement. However, these treatments can be inconvenient and are often ineffective or only partially effective at reducing symptoms, and are temporary. Analgesics have also been utilized to treat symptoms of engorgement but their effectiveness has not been verified. Another treatment that has been utilized to treat symptoms of breast engorgement is the application of cabbage leaves to the breast. This treatment can also be inconvenient and has proven to have limited success.

It would be advantageous to provide alternative methods and treatments for alleviating breast engorgement.

SUMMARY OF THE INVENTION

In one aspect the invention includes a pad for relieving breast engorgement. The pad includes a material comprising absorbent fibers and an acidic agent. The pad is configured to insert within the cup of a bra.

In one aspect the invention includes a bra pad having a layer of absorbent fiber material with a front surface and a back surface. A liquid barrier layer has a first side interfacing the back surface of the absorbent fiber material and an opposing second side. An acidic agent is disposed within the absorbent fiber material.

In one aspect the invention includes a method of relieving breast engorgement. The method includes providing an absorbent pad including absorbent fibers and an acidic agent, shaped to insert within a cup of a bra. The pad is disposed between the cup of the bra and an engorged breast to be relieved.

BRIEF DESCRIPTION OF THE DRAWINGS

Preferred embodiments of the invention are described below with reference to the following accompanying drawings.

FIG. 6 is a diagrammatic representation of a bra pad in accordance with one aspect of the invention inserted between a bra and a woman's breast.

FIG. 7 is a diagrammatic side view of a bra pad in accordance with another embodiment of the invention.

FIG. 8 is a top view of a pad in accordance with an additional aspect of the invention.

FIG. 9 is a cross-sectional view of the pad shown in FIG. 8 pad taken along line 9-9 of FIG. 8.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general the invention encompasses methods and articles for relieving breast engorgement. Breast engorgement can occur in one or both breasts. Although the invention is described as treating an individual breast it is to be understood that the invention contemplates simultaneous treatment of both breasts.

Specifically, the invention includes pads for relieving breast engorgement and methodology for relieving breast engorgement, which can utilize pads of the invention. The invention can effectively alleviate symptoms of breast engorgement including pain, breast swelling, hardness, heat and/or throbbing. Methodology in accordance with the invention can be advantageous when utilized during weaning or when a mother chooses not to breastfeed her newborn since particular applications of the invention can accelerate cessation of lactation in addition to alleviating symptoms of breast engorgement. Due to these effects, methodology of the invention can additionally be utilized for treating symptoms of galactorrhea, the production of milk unrelated to pregnancy or nursing.

Figure 1:
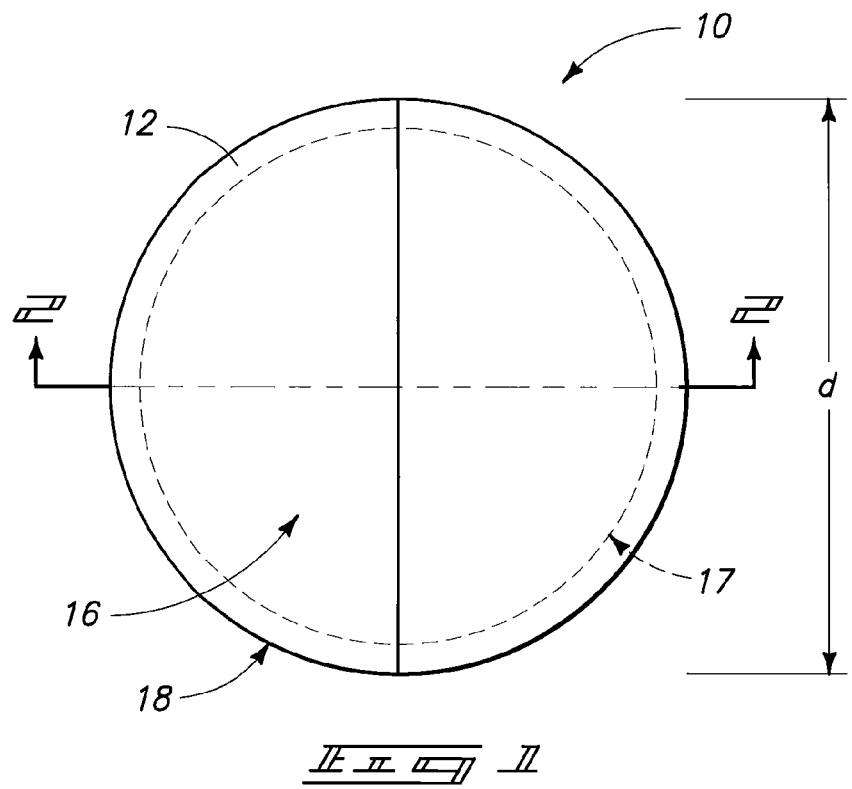
FIG. 1 is a top view of a bra pad in accordance with one aspect of the invention.

Aspects of the invention are described generally with reference to FIGS. 1-7. Referring initially to FIG. 1, such shows a pad 10 having a top surface 12 with an innermost portion 16 (surrounded by dashed line 17). Pad 10 is surrounded by perimeter 18. Innermost region 16 of pad 10 contains an acidic agent. The acidic agent can be, for example an acid fruit juice such as juice from lemon, lime, orange, tangerine, mango, green apple, grapefruit, pineapple, tomato, passion fruit, grape, cranberry, pomegranate, etc. or combinations thereof. Alternatively the acidic agent can be an acidulant, commonly utilized to give a sharp taste to foods. Acidulants which can be utilized as acidic agents for purposes of the invention include but are not limited to citric acid, adipic acid, tartaric acid, lactic acid, glucono delta lactone (GDL), malic acid, fumaric acid, phosphoric acid and acetic acid, and combinations thereof. Further, the invention encompasses utilization of organic carboxylic acids having up to 10 carbon atoms, preferably up to six carbon atoms. A combination of one or more fruit juices, acidulants and/or carboxylic acids can also be utilized. The pH of the acidic agent is not limited to any particular value. In particular applications, the pH of the acidic agent can be from about pH 3.7 to about pH 5. An appropriate buffer (such as a phosphate buffer) can be utilized to maintain the pH within the desired range, and base such as bicarbonate can be utilized to achieve the pH within the desired range, as applicable.

The size of innermost portion 16 is not limited to a particular relative area of the pad and is illustrated for example purposes only. It is to be understood that portion 16 can be smaller or larger relative to pad 10 as compared to the relative sizes shown. For example, in particular embodiments region 16 can extend to the perimeter of pad 10 and line 17 can coincide with perimeter line 18. Alternatively, portion 16 can be smaller than the relative size indicated, so long as an innermost portion of pad 10 contains the acidic agent.

Figure 2:
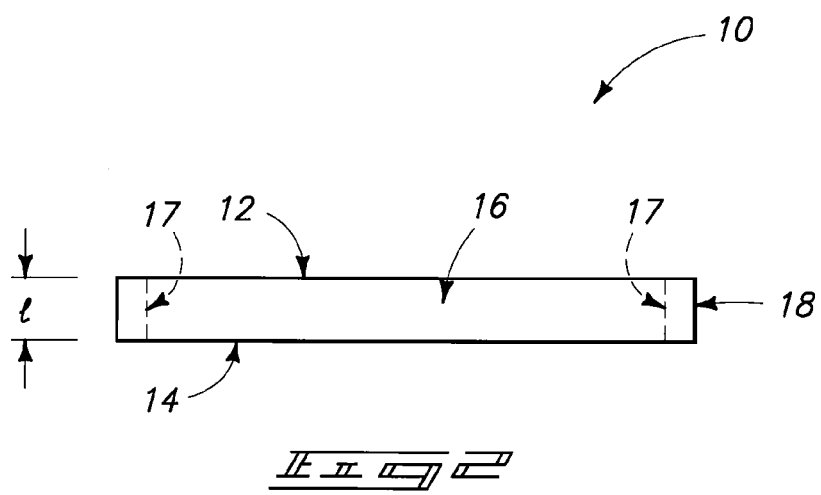
FIG. 2 is a cross-sectional view of the bra pad shown in FIG. 1 taken along line 2-2 of FIG. 1.

Referring to FIG. 2, such shows a cross-section view taken along line 2-2 of FIG. 1. As indicated in FIG. 2, dashed line 17 extends from top surface 12 of pad 10 to an opposing bottom surface 14. Such is utilized to indicate the acidic agent extending throughout the depth ρ of pad 10. It is to be understood however, that the invention contemplates aspects where the acidic agent is provided, at least initially, within only an upper portion of pad 10 (not shown).

Pad 10 can preferably comprise one or more absorbent, fibrous materials. The fibers within such material can be, for example, randomly oriented fibers, oriented fibers, spun fibers, woven fibers, non-woven fibers, or combinations thereof. Example absorbent fibers that can be utilized include natural fibers and/or synthetic fibers. Example natural fibers include, but are not limited to, cotton fibers and cellulose or other polysaccharide fibers. Example synthetic fibers include, for example, thermoplastic fibers.

Referring again to FIG. 1 a circular shaped pad is illustrated. It is to be understood that the illustrated shape is but one example and that pad 10 can be an alternative shape such as, for example, rectangular, square, oblong, oval, hemispherical, etc. It can be preferable for pad 10 to be circular to allow the pad to conform to the shape of a woman's breast.

Pad 10 is not limited to a particular size. Where pad 10 is circular, pad 10 can preferably have a diameter of from about 3.5 inches to about 4 inches. A smaller or larger diameter pad can be utilized for a smaller or larger bra cup size. In particular instances, pad 10 will have a diameter of about four inches.

Referring again to FIG. 2, thickness ρ of pad 10 is not limited to a particular value and can be from about 0.25 inches to about 0.5 inches. In particular instances, the pad thickness can preferably be 0.5 inches.

The amount of acidic agent contained in pad 10 will be dependent upon the size and thickness of the pad. For a four inch diameter circular pad having a thickness of about 0.5 inches, a preferred amount of acidic agent can be about 15 ml. However the invention contemplates utilization of from about 15 ml to about 30 ml of acidic agent for this size pad. Alternative size pads can contain a greater or lower amount of acidic agent.

In particular instances, the acidic agent can be provided within the pad in powdered form. Hydration of the pad can be conducted prior to use with an amount of water depending upon pad size as set forth above.

Pads in accordance with the invention can be preserved by freezing (discussed below). Alternatively or additionally, the acidic agent within the pad can contain one or more preservatives to prolong the shelf life of the pad. Where the acid agent is provided in powdered form the freezing can be eliminated if desired.

Figure 3:
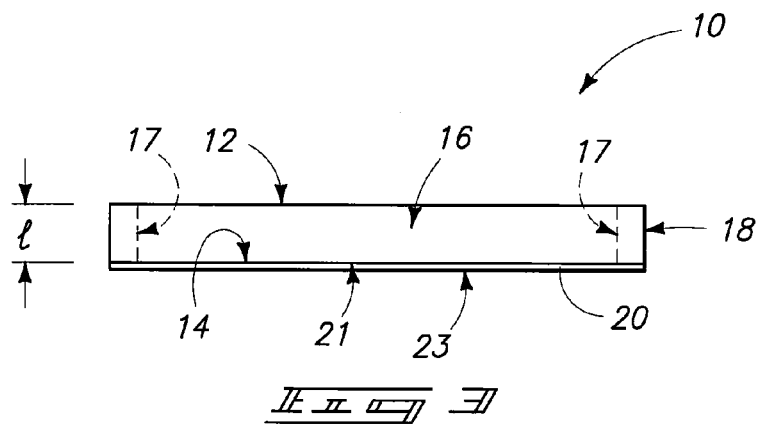
FIG. 3 is a cross-sectional view of a bra pad in accordance with an alternative aspect of the invention.

Referring next to FIG. 3, such shows an alternative aspect of the invention relative to that depicted in FIGS. 1-2. As illustrated, pad 10 can comprise a liquid barrier layer 20 having a first side 21 interfacing bottom surface 14 of the absorbent fiber material of pad 10. Liquid barrier layer 20 can be a plastic backing material and can comprise, for example, polypropylene or alternative plastic. It can be advantageous to provide a liquid barrier to limit or prevent acidic agent from escaping pad 10 through the bottom surface and/or absorbing into adjacent materials such as material of a bra (discussed below).

Figure 4:
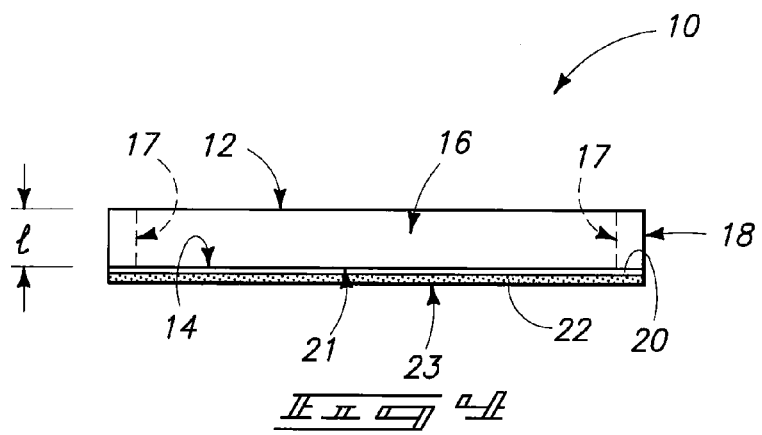
FIG. 4 is a cross-sectional view of a bra pad in accordance with an additional alternative aspect of the invention.

Referring next to FIG. 4, such shows an additional alternative embodiment of the present invention. As illustrated in FIG. 4, pad 10 includes a liquid barrier layer 20 and additionally includes an adhesive material 22 disposed on back surface 23 of liquid barrier 20. In embodiments which lack liquid barrier layer 20, such as that illustrated in FIGS. 1-2, adhesive material 22 can be directly against bottom surface 14 of pad 10 (not shown).

Figure 5:
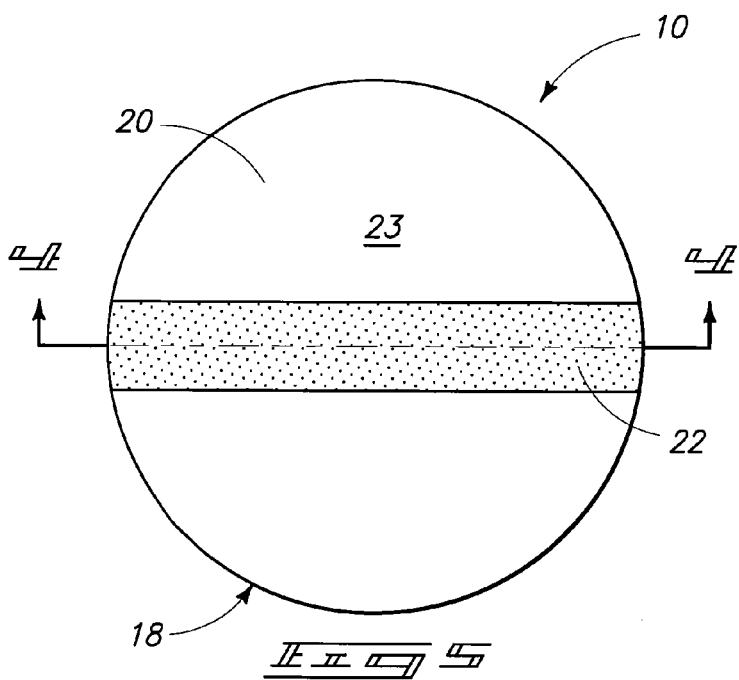
FIG. 5 is a bottom-view of the pad shown in FIG. 4, with FIG. 4 being taken along line 4-4 of FIG. 5.

Preferably adhesive material 22 can be a reversible adhesive such that pad 10 can be reversibly adhered with the cup of a bra (discussed below). Referring to FIG. 5, such shows a bottom view of the embodiment of pad 10 depicted in FIG. 4 with FIG. 4 being taken along line 4-4 of FIG. 5. As illustrated in FIG. 5, adhesive material 22 can be a strip of adhesive material disposed on the second side 23 of the liquid barrier layer 20. Adhesive material 22 can extend across the entire diameter of pad 10 to perimeter 18 as illustrated, or alternatively can extend less than the entire diameter (not shown). In alternative aspects, adhesive material 22 can cover an entirety of the second side 23 of liquid barrier layer 20 (or bottom surface 14 where barrier layer 20 is absent) or can comprise multiple strips or a circular patch, for example (not shown). For packaging purposes, adhesive material 22 can be covered with a paper or plastic pull-off strip or sheet which can be removed prior to adhering pad 10 to the inner surface of a bra.

As illustrated in FIG. 6, pad 10 is configured to be inserted between a bra 50 and a breast 62 of a woman 60. Pad 10 is inserted within a cup 52 of bra 50 such that bottom side 14 of pad 10 interfaces the inside of cup 52 and top side 12 of pad 10 is against the woman's breast. In embodiments where pad 10 includes an adhesive material (discussed above), the adhesive material can be utilized to position pad 10 within cup 52 by pressing the pad within cup 52. Preferably, bra 50 is a well fitting bra, such that pad 10 is held securely in place while being worn between the breast and the bra.

Referring to FIG. 7, such shows an additional embodiment according to the invention. As depicted in FIG. 7, circular pad 10 can be rendered concave shaped. Such can be achieved by, for example, providing one or more folds, creases, pleats and/or seams as represented by features 26. In particular instances the one or more folds, creases, pleats and/or seams will extend from perimeter 18 partially inward toward the radial center of pad 10 as illustrated. The resulting concave shape can help pad 10 conform to the shape of a woman's breast and help retain pad 10 between a bra and the breast to be relieved.

Another aspect of the invention is depicted in FIGS. 8-9. Features of the invention that correspond generally to features described above are given the same numeric identifier utilized earlier followed by the subscript "a". New features are assigned new identifiers. The pad 10a depicted in FIG. 8 has a central area bounded by line 18a. Such area corresponds to a pad area similar to pad 10 illustrated and described with reference to FIGS. 1-2. Such central region may include all the features and alternatives described above. Pad 10a of FIG. 8 additionally has an outer peripheral region 32 which extends from line 18a to an outer edge 30 of pad 10a.

Referring to FIG. 9, such shows a cross section of pad 10a taken along line 9-9 of FIG. 8. As shown, outer peripheral region 32 can be tapered from line 18a to edge 30. As indicated above, the central portion within line 18a can have a preferred thickness of from 0.25-0.5 inches. Tapered region 32 can preferably taper from the thickness at line 18a to a final thickness of about 0.125 inches at edge 30.

As indicated above, the central region bounded by line 18a can preferably have a diameter da of about 4 inches. An overall diameter of pad 10a can be from between greater than 4 inches to about 8 inches. The diameter of pad 10a can be based upon bra cup size, for example, where an 8 inch diameter pad would be appropriate for a C to D or larger bra cup size.

Peripheral region 32 can comprise any of the absorbent materials set forth above. It can be preferable that peripheral region 32 comprise the same material that the central pad region contains. Pad 10a can further comprise a liquid barrier layer and/or an adhesive material as described above. Pad 10a can further include one or more of folds, creases, pleats and/or seams as represented by features 26 of FIG. 7.

Methodology in accordance with the invention includes providing an absorbent pad such as any of those described above comprising absorbent fibers and an acidic agent, shaped to insert within the cup of a bra. The absorbent pad is disposed between the cup of a bra and an engorged breast to be relieved as depicted in FIG. 6. Where the pad comprises an adhesive, disposing the pad between the breast and the bra may include pressing the adhesive to an inner surface of the cup of the bra.

Each pad may be worn for a period of up to about 4 hours. The first pad may then be replaced with a second pad and so on, with replacement periodically over a period of about from 4 to about 5 days, or until breast engorgement is fully relieved.

Pads of the present invention may be stored frozen for a period of months. Accordingly, methodology for use may include thawing, or at least partially thawing the pad prior to inserting the pad between the cup of a bra and the breast. In particular instances, it may help alleviate symptoms such as pain and swelling to apply the pad while in a partially frozen state.

Figure 10:
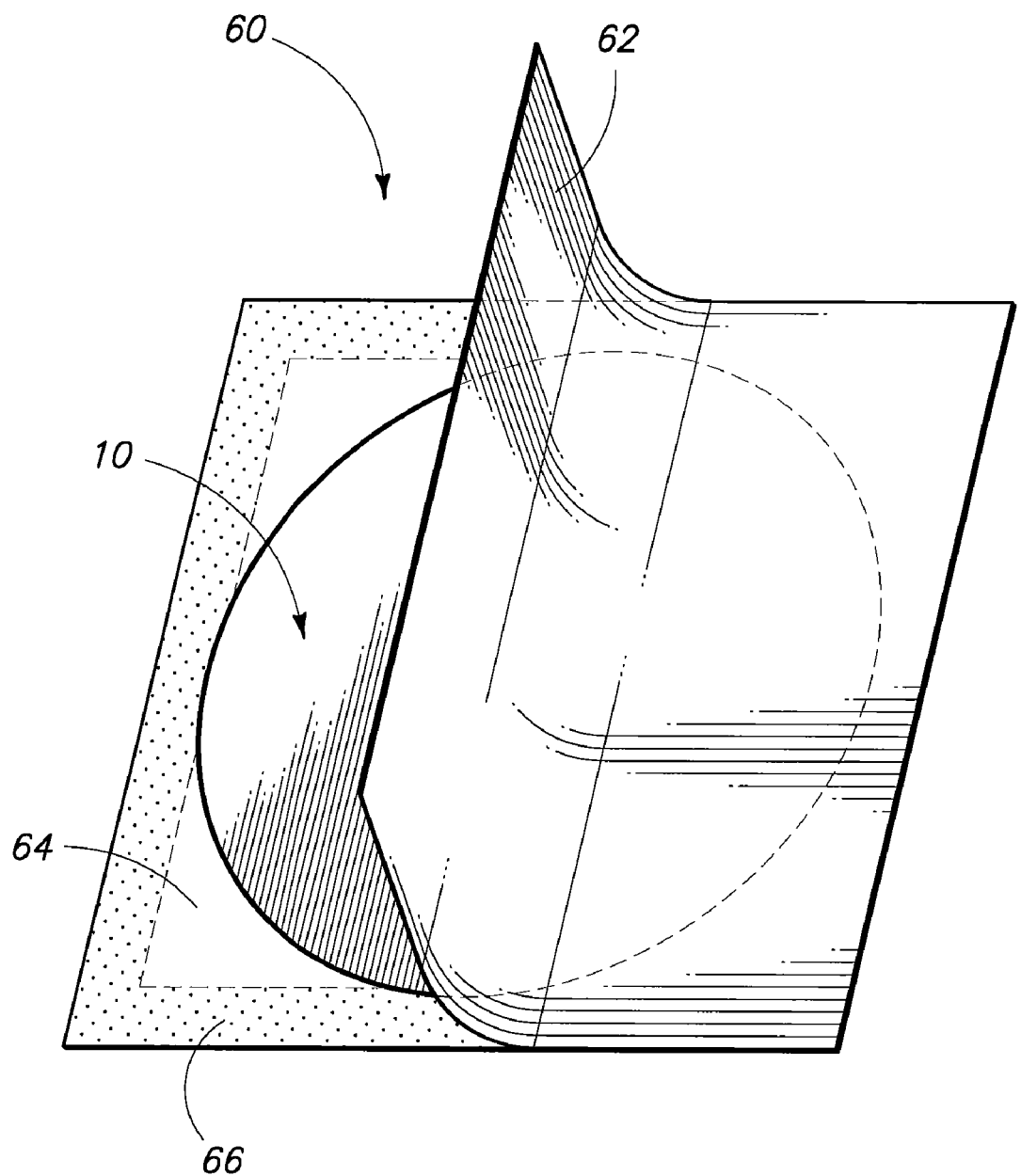
FIG. 10 is a diagrammatic view of a packaged pad in accordance with one aspect of the invention.

Referring next to FIG. 10, such depicts an example packaging aspects in accordance with the invention. Packaging 60 is provided to enclose pad 10 for shipment and/or storage. Packaging 60 can comprise one or more foil sheets 62, 64 which are held together by at least one seal 66. Seal 66 is preferably an air-tight seal and can comprise an adhesive, a weld, a vacuum seal, or other appropriate seal or combination thereof. Preferably seal 66 comprises a pull-apart vacuum seal as illustrated. Once foil sheets 62, 64 have been vacuum sealed, the sealed package can be frozen and stored until ready for use.

Vacuum sealed packages 60 can be provided individually or can be provided in a group. Where a group of pads is provided together, individual packages 60 may be stacked and provided in a cylindrical carton or other container (not shown).

Methodology of the invention can advantageously relieve symptoms of breast engorgement. Further, methodology can accelerate cessation of lactation to thereby eliminate the cause of breast engorgement. Treatment in accordance with the invention can also be utilized to prevent breast engorgement. For example, if a mother to be chooses not to breast feed her baby, the pads may be applied prior to engorgement, beginning as within 24 hours after delivery, in order to halt lactation. Accordingly, the articles and methodology of the invention are distinctly advantageous relative to conventional methodology for the treatment of breast engorgement.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A pad for relieving breast engorgement, comprising:
a material comprising absorbent fibers; and
from about 15 ml to about 30 ml of an acidic agent to decrease breast engorgement within the absorbent fibers, the acidic agent being selected from the group consisting of acidic fruit juices, citric acid, adipic acid, tartaric acid, lactic acid, glucono delta lactone (GDL), malic acid, fumaric acid, phosphoric acid, acetic acid and carboxylic acids having ten or fewer carbon atoms, and combinations thereof; the pad being configured to insert within the cup of a bra.

2. The pad of claim 1, wherein the pad contains about 15 ml of the acidic agent.

3. The pad of claim 1 wherein the pad is circular shaped.

4. The pad of claim 3 wherein the pad comprises a plurality of one or more member of the group consisting of creases, pleats, folds and seams.

5. The pad of claim 3 wherein the pad comprises an outer peripheral region that is tapered in thickness.

6. The pad of claim 1 wherein the material comprises woven fibers.

7. The pad of claim 1 wherein the material comprises non-woven fibers.

8. The pad of claim 1 wherein the absorbent fibers comprise one or more members of the group consisting of cotton fibers, polysaccharide fibers and synthetic fibers.

9. The pad of claim 1 further comprising a liquid barrier material layer.

10. The pad of claim 9 wherein the liquid barrier material comprises plastic.

11. The pad of claim 1 further comprising an adhesive material.

12. A bra pad comprising:
a layer of absorbent fiber material having a front surface and a back surface;
a liquid barrier layer having a first side interfacing the back surface of the absorbent fiber material, and an opposing second side; and
from about 15 ml to about 30 ml of an acidic agent within the absorbent fiber material to decrease breast engorgement, the acidic agent being selected from the group consisting of acidic fruit juices, citric acid, adipic acid, tartaric acid, lactic acid, glucono delta lactone (GDL), malic acid, fumaric acid, phosphoric acid, acetic acid, and carboxylic acids having ten or fewer carbon atoms, and combinations thereof, disposed within the absorbent fiber material.

13. The bra pad of claim 12 further comprising an adhesive material disposed on the second side of the liquid barrier layer, the adhesive material being configured to reversibly attach the pad within a cup of a bra.

14. The bra pad of claim 12 wherein the absorbent fiber material comprises woven fibers, non-woven fibers, or both woven and non-woven fiber, the woven and non-woven fibers comprising fibers selected from the group consisting of cotton fibers, polysaccharide fibers and synthetic fibers.

15. A packaged bra pad comprising the bra pad of claim 12 wherein the pad is packaged individually in a vacuum-sealed package.

16. The bra pad of claim 12 wherein the pad is frozen.

17. The packaged bra pad of claim 15 wherein the pad is packaged in a foil packaging material configured to open by pulling apart a one or more seals between the foil packaging material.

18. A method of preventing or relieving breast engorgement, comprising:
  providing an absorbent pad comprising absorbent fibers and from about 15 ml to about 30 ml of an acidic agent within the absorbent pad to decrease breast engorgement, the absorbent pad being shaped to insert within a cup of a bra;
  disposing the absorbent pad between the cup of the bra and an engorged breast to be relieved.

19. The method of claim 18 wherein the acidic agent is selected from the group consisting of acidic fruit juices, citric acid, adipic acid, tartaric acid, lactic acid, glucono delta lactone (GDL), malic acid, fumaric acid, phosphoric acid, acetic acid, carboxylic acids having ten or fewer carbon atoms, and combinations thereof.

20. The method of claim 18 wherein the disposing comprises pressing an adhesive comprised by the pad to an inner surface of the cup of the bra.

21. The method of claim 18 wherein the providing the absorbent pad comprises providing the absorbent pad in a frozen state and at least partially thawing the pad from the frozen state.

22. The method of claim 18 wherein the pad is circular shaped.

23. The method of claim 22 wherein the circular shape is concave.

24. The method of claim 23 wherein the pad comprises a one or more folds, creases, pleats and/or seams.

25. The method of claim 18 wherein the pad is a first pad and further comprising providing a second pad and replacing the first pad with the second pad after the first pad has been worn for about 4 hours.

26. The method of claim 18 wherein the pad is a first pad and further comprising providing a plurality of additional pads, wherein the first pad is replaced periodically with additional pads over a period of from about 4 days to about 5 days, or until breast engorgement is relieved and/or lactation has ceased.

* * * * *

UNITED STATES PATENT AND TRADEMARK OFFICE
CERTIFICATE OF CORRECTION

PATENT NO.       : 8,142,255 B2
APPLICATION NO.  : 12/476493
DATED            : March 27, 2012
INVENTOR(S)      : Sharon Johnston It is certified that error appears in the above-identified patent and that said Letters Patent is hereby corrected as shown below:

Column 2, line 17 – Replace "pad taken" with --taken--

Column 3, line 20 – Replace "depth ρ of" with --depth $\ell$ of--

Column 3, line 44 – Replace "thickness ρ of" with --thickness $\ell$ of--

Column 5, line 9 – Replace "diameter da of" with --diameter $d_a$ of--

Column 5, line 19-20 – Replace "Pad 10 a can" with --Pad 10*a* can--

Signed and Sealed this
Fourteenth Day of August, 2012

David J. Kappos
*Director of the United States Patent and Trademark Office*